United States Patent [19]

Leute et al.

[11] 4,197,237

[45] Apr. 8, 1980

[54] ANTIBODIES TO NITROGEN DERIVATIVES OF BENZOYL ECGONINE ANTIGENIC CONJUGATES THEREOF

[75] Inventors: Richard K. Leute, Sunnyvale; Gunner Bolz, Woodside, both of Calif.

[73] Assignee: Syva Company, Palo Alto, Calif.

[21] Appl. No.: 549,262

[22] Filed: Feb. 12, 1975

Related U.S. Application Data

[62] Division of Ser. No. 365,915, Jun. 1, 1973, Pat. No. 3,888,866.

[51] Int. Cl.$^2$ .................... C07G 7/00; G01N 31/00; G01N 33/16
[52] U.S. Cl. ........................... 260/112 B; 260/112 R; 260/112.5 R; 260/121; 424/1; 424/8; 424/12; 424/85; 424/177
[58] Field of Search .................. 424/1, 8, 12, 85, 177; 195/63, 103.5 A; 260/112 R, 112 B, 112.5, 121, 78 A; 528/331, 327

[56] References Cited

U.S. PATENT DOCUMENTS

| | | | |
|---|---|---|---|
| 3,690,834 | 9/1972 | Goldstein | 424/12 X |
| 3,852,157 | 12/1974 | Rubenstein | 424/12 X |
| 3,966,764 | 6/1976 | Goldstein | 424/2 |
| 3,975,237 | 8/1976 | Rubenstein | 195/63 |
| 4,022,878 | 5/1977 | Gross | 424/12 X |

*Primary Examiner*—Anna P. Fagelson
*Attorney, Agent, or Firm*—Bertram I. Rowland

[57] ABSTRACT

Nitrogen derivatives of benzoyl ecgonine and cocaine are provided, particularly amino, diazonium, and diazo derivatives, the compounds finding use either directly or as intermediates for the preparation of reagents for use in immunoassays. Diazo compounds can be coupled with antigenic materials for the preparation of antibodies to benzoyl ecgonine and/or cocaine. The amino group can be combined with active non-oxo-carbonyl compounds to form reagents which find use in immunoassays.

5 Claims, No Drawings

ANTIBODIES TO NITROGEN DERIVATIVES OF BENZOYL ECGONINE ANTIGENIC CONJUGATES THEREOF

This is a division, of application Ser. No. 365,915, filed June 1, 1973, now U.S. Pat. No. 3,888,866.

BACKGROUND OF THE INVENTION

1. Field of the Invention

A wide variety of ways have been developed for determining minute quantities of various organic compounds. A number of methods which can be used for the determination of organic compounds depend on the availability of a receptor which recognizes a particular compound or class of compounds. The most common type of receptor is the antibody which is able to strongly bind to a particular spatial conformation and polar or non-polar distribution.

In order to prepare the antibodies for compounds which are not antigenic, the non-antigenic compound is normally bonded to an antigenic material, particularly a protein. With most compounds, it is found necessary to modify the compound of interest to bond to the antigen.

In addition, in some of the immunoassays, it is necessary to bond the compound to a detector molecule. The link that is chosen for bonding to the antigen and to the detector molecule must allow not only for satisfactory bonding to the various molecules, but also must provide an antibody which recognizes the compound when it is bound to the detector molecule.

In addition, the linking group must not significantly change the polar characteristics of the compound to be assayed nor detrimentally affect the molecules to which the compound is bonded. Depending on the particular material to which the compound is to be bonded, the linking group should permit a sufficient number of the desired compound to be bonded to the antigen or detector molecule. Additional considerations include synthetic simplicity, chemical stability, the effect of the bonding functionality on the material to which it is bonded, and the particular site on the material, for example, a protein, to which the compound will be bonded.

2. Description of the Prior Art

An immunoassay technique employing a stable free radical detector, entitled FRAT$^R$, supplied by Syva Corporation, is described in U.S. Pat. No. 3,690,834. Another immunoassay technique using enzymes as a detector and commercially available as EMIT$^{TM}$, supplied by Syva Corporation, is found in copending application, Ser. No. 143,609 filed May 14, 1971. Radioimmunoassay is described in a number of texts for example Kirkham, et al, Radioimmunoassay Methods, Churchill, Livingston, London, 1971. A description of a number of derivatives of cocaine and ecgonine may be found in Pelletier, Chemistry of the Alkaloids, Van Nostrand-Reinholt, New York 1970. U.S. Pat. No. 3,498,989 also discloses a number of cocaine derivatives. Odell, Competitive Protein Binding, Blackwell Scientific Publications, Oxford 1971, Chapter II, page 25, describes various methods of conjugating haptens to antigens.

SUMMARY OF THE INVENTION

Cocaine and benzoyl ecgonine derivatives are provided having nitrogen containing substituents bonded to an aromatic carbon atom. The nitrogen is present as amino, diazo and diazonium groups which can be used for conjugation or are conjugated to antigenic proteins for the formation of antibodies or to a detector molecule to provide reagents for use in immunoassays. In particular, the amino compounds can be combined with non-oxo-carbonyl derivatives to provide amides or amidines for use as the reagents.

Description of the Specific Embodiments

The compounds of this invention are derivatives of nor-tropane which are able to be used for preparing antibodies to benzoyl ecgonine, a metabolite of cocaine, or cocaine, as well as be bonded to detector molecules for use in immunoassays.

Ecgonine is a 2-carboxy-3-hydroxytropane. Cocaine is the methyl ester of 2-carboxy-3-hydroxytropane benzoate. The derivatives of this invention will either be at the 3 position or the 8 position of the nor-tropane ring.

For the most part, the compounds of this invention will be of from 16 to 23 carbon atoms. Excluding the anion of the diazonium salt, the compounds will normally have from 4 to 7 heteroatoms which are oxygen and nitrogen, prior to their conjugation to a poly(amino acid)—polypeptides and proteins—or detector molecule. For the most part, the compounds will have from 3 to 4 oxygen atoms, usually 4 oxygen atoms, and from 2 to 3 nitrogen atoms.

The compounds can be prepared as the amines or the ammonium halide salt, e.g., hydrochlorides, normally having 1-2 hydrohalides per molecule. Therefore, the compounds employed as intermediates for conjugation also include their respective hydrohalide salts.

The compounds of this invention will, for the most part, have the following formula:

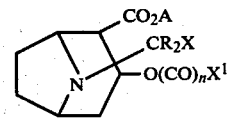

wherein:
A is hydrogen or methyl, preferably hydrogen;
R is hydrogen or alkyl of from 1 to 3 carbon atoms, e.g., methyl, usually hydrogen.
X is hydrogen or $\phi$-Y;
$X^1$ is hydrogen, phenyl or $\phi$-Y;
$\phi$ is phenylene
n is zero when $X^1$ is hydrogen and is one when $X^1$ is other than hydrogen; and
Y is amino or diazonium having a neutral or weakly basic counterion, e.g., halide, sulfate, arylsulfonate and the like;
there being only one -$\phi$-Y per molecule.

When the nitrogen functionality is substituted at the 8 position, the compounds will, for the most part, have the following formula:

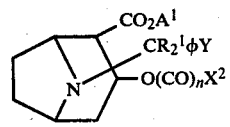

wherein:
$A^1$ is hydrogen or methyl;
$\phi$ is phenylene;
$R^1$ is hydrogen or alkyl of from 1 to 3 carbon atoms, e.g., methyl preferably hydrogen;

$X^2$ is hydrogen or phenyl n is zero when $X^2$ is hydrogen and one when $X^2$ is phenyl Y is amino or a diazonium salt having a neutral or weakly basic counterion.

When the nitrogen substituent is at the 3 position, the compounds will, for the most part, have the following formula:

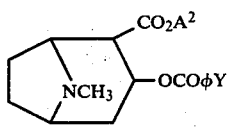

wherein:

$A^2$ is hydrogen or methyl;

$\phi$ is phenylene; and

Y is amino or a diazonium salt having a weakly basic or neutral counterion.

The substituents on the phenyl rings will be meta- or para-, i.e., separated by at least 3 carbon atoms.

Illustrative compunds include:

meta-aminobenzoylecgonine methyl ester;

N-(para-amino-alpha,alpha-dimethylbenzyl)norecgonine;

N-(para-diazonium-alpha,alpha-dimethylbenzyl)norecgonine methyl ester chloride;

para-diazonium benzoylecgonine methyl ester tolylsulfonate;

N-(meta-diazonium-alpha,alpha-dimethylbenzyl)norecgonine methyl ester benezene sulfonate; and meta-diazoniumbenzoylecgonine methyl ester bromide Of particular interest are the amino or diazonium groups bonded to a poly(amino acid)—polypeptide or protein—structure. One group of poly(amino acids) is antigenic, so that by bonding the nitrogen modified cocaine, ecgonine or benzoyl ecgonine to the poly(amino acid), antibodies can be formed to cocaine and its metabolites. A narrower class of poly(amino acids) which can also be used as antigens, but will not normally be used as such, are enzymes which are employed as the detector in an immunoassay system.

Polypeptides usually encompass from about 2 to 100 amino acid units (usually less than about 12,000 molecular weight). Larger polypeptides are arbitrarily called proteins. Proteins are usually composed of from 1 to 20 polypeptide chains, called subunits, which are associated by covalent or non-covalent bonds. Subunits are normally of from 100 to 300 amino acid groups (approximately 10,000 to 35,000 molecular weight). For the purposes of this invention, poly (amino acid) is intended to include individual polypeptide units, or polypeptides which are subunits of proteins, whether composed solely of polypeptide units or polypeptide units in combination with other functional groups, such as porphyrins, as in hemoglobin or cytochrome oxidase.

The first group of poly(amino acids) which will be considered are the antigenic poly(amino acids). These may be joined directly to the cocaine derivative by means of the diazonium group or indirectly by initial substitution of dibasic acid to the amino group, followed by conjugation of the remaining carboxylic acid group to an amino group of the poly(amino acid). The resulting product can be used for the formation of antibodies to cocaine and/or its metabolites.

With most conventional poly(amino acids) employed as antigens, there will not be more than about one cocaine or derivative group per 1,500 molecular weight, usually not more than one group per 2,000 molecular weight. There will be at least one group per 500,000 molecular weight, usually at least one per 50,000 molecular weight. With intermediate molecular weight antigens (50,000 to 1 million) the number of cocaine or derivative groups will generally be from about 2 to 250, usually from 2 to 10, more usually 10 to 100.

With low molecular weight antigens, 1,000 to 5,000, the number of cocaine or derivative groups will be in the range of 1 to 10, usually in the range of 2 to 5, so that there may be as many as one cocaine or derivative per 500 molecular weight of poly(amino acid).

Usually, the number of groups bonded to the poly(amino acid) will be related to the available amino groups, e.g., the number of lysines present. Depending on the conditions of coupling of the diazonium compound, various other functionalities normally present in poly(amino acids) also provide sites of conjugation to the diazonium group. These include activated aromatic rings such as are present in tyrosine, heterocyclic rings, such as are present in tryptophane, proline and histidine, and the like. The amino containing amino acids include lysine and arginine.

Various protein types may be employed as the antigenic material. These types include albumin, serum proteins, e.g., globulins, ocular lens proteins, lipoproteins, etc. Illustrative proteins include bovine serum albumin, key-hole limpet hemocyanin, egg ovalbumin, bovine $\gamma$-globulin, etc. Small natural polypeptides which are immunogenic, such as gramicidin may also be employed. Various synthetic poly(amino acids) may also be employed, such as polymers of lysine, glutamic acid, phenylalanine, tryosine, etc., either by themselves or in combination. Of particular interest is polylysine or a combination of lysine and glutamic acid. Any synthetic polypeptide must contain a sufficient number of active groups, as for example, amino groups provided by lysine.

The second group of poly(amino acids) are the enzymes to which the nitrogen substituted derivates may be conjugated. As indicated, the cocaine derivative modified enzyme is useful for immunoassays. The immunoassay technique will follow in greater detail.

Various enzymes may be used such as oxidoreductases, hydrolases, lyases, and the like. These enzymes include esterases, amidases, phosphorylases, carbohydrases, oxidases, reductases and the like. Of particular interest are such enzymes as lysozyme, amylase, dehydrogenases, particularly malate dehydrogenase, lactate dehydrogenase, mannitol-1-phosphate dehydrogenase, and glucose 6-phosphate dehydrogenase, $\beta$-glucuronidase, cellulase and, phospho-lipase, particularly phospholipase C. The enzymes will usually have molecular weights in the range of about $1 \times 10^4$ to $6 \times 10^5$, more usually in the range of about $1.2 \times 10^4$ to $3 \times 10^5$.

There will usually be at least one cocaine or derivative group per enzyme molecule, and usually not more than one group per 1,500 molecular weight, usually not more than one group per 2,000 molecular weight. Usually there will be at least one cocaine or derivative group per 50,000 molecular weight, and more usually at least one group per 30,000 molecular weight. The modified enzyme will retain on the average at least 10%, more usually at least 30% of the original activity of the unmodified enzyme.

Where the cocaine or derivative is bonded to a polypeptide, there need be only one cocaine or derivative group, but usually there will be at least two groups. With the enzymes the number of cocaine or derivative groups will generally be of from 1 to 30, more usually 2 to 25. Usually there will be at least 2, more usually at least 3, groups per enzyme, when the enzyme is randomly substituted with the cocaine or derivative groups and preferably not more than 16.

The substituted polypeptides will, for the most part, have the following formulae:

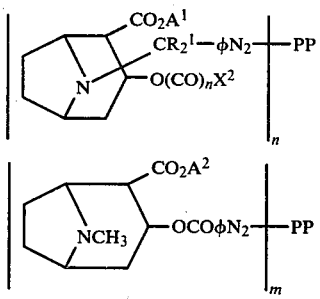

wherein:

$A^1$ and $A^2$, $R^1$, $X^2$, $\phi$, and n have all been defined previously, m is the number of groups bonded to PP and PP is the polypeptide. Where PP is an enzyme, m will normally be in the range of about 1 to 30, usually in the range of 1 to 25 and more usually in the range of 2 to 16. When PP is an antigenic poly(amino acid), m will generally be in the range of 1 to 500, usually 10 to 200, depending on the molecular weight of PP.

Instead of an enzyme, a stable free radical may be employed as a functionality for detection in the immunoassay. These stable free radicals are cyclic nitroxides, having the nitrogen of the nitroxide as an annular member and from 0 to 1 other heteroatoms, i.e., oxygen and nitrogen, as annular members.

The spin labeling molecules bonded to the derivatives of cocaine or ecgonine will normally be of 8 to 16 carbon atoms, usually of from 8 to 12 carbon atoms. The functionality for linking to the cocaine or ecgonine derivative will be bonded directly to the amino group, normally through a non-oxo-carbonyl group, e.g., carboxyl. The non-oxo-carbonyl group may be bonded directly through an annular carbon atom or bonded through an aliphatic chain to an annular carbon atom, the chain normally being of from about 1 to 4 carbon atoms, usually of from 1 to 2 carbon atoms. The molecules may have from 0 to 2 sites of ethylenic unsaturation, more usually from 0 to 1 site of ethylenic unsaturation.

For the most part, stable nitroxide free radical functionalities which are employed will have the following formula:

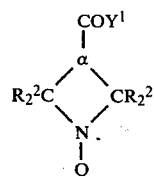

wherein:

α is a divalent aliphatic radical, having from 0 to 1 site of aliphatic unsaturation, usually aliphatically saturated of from 1 to 6 carbon atoms, usually from 2 to 3 carbon atoms being annular atoms;

$R^2$ is lower alkyl (1 to 6, usually 1 to 3 carbon atoms), and preferably methyl; and $Y^1$ is one of the following formulae:

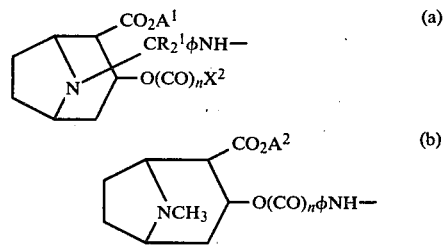

wherein:

$A^1$, $A^2$, $R^1$, $X^2$, n and $\phi$ have been previously defined.

For the most part, and cyclic nitroxides are pyrrolidine or piperidine derivatives.

Illustrative spin labeled compounds include:

N-(alpha-[N'-(O$^3$-benzoyl nor-ecgoninyl)]-para-tolyl) 1-oxyl-2,2,5,5-tetramethyl-3-pyrrolinyl-3-formamide;

N-(alpha-[N'-(O$^3$-benzoyl nor-ecgoninyl methyl ester)]-para-cumyl)1-oxyl-2,2,6,6-tetramethyl-4-piperidinylformamide;

N-(alpha-[N'-(O$^3$-benzoyl nor-ecgoninyl methyl ester)]-meta-tolyl)1-oxyl-2,2,5,5-tetramethyl-3-pyrolidinylformamide;

N-(1-oxyl-2,2,5,5-tetramethyl-3-pyrrolidinylformyl) para-aminobenzoylecgonine methyl ester;

N-(1-oxyl-2,2,6,6-tetramethyl-4-piperidinylformyl) meta-aminobenzoylecgonine methyl ester; and N-(1-oxyl-2,2,5,5-tetramethyl-3-pyrrolinyl-3-formyl) para-aminobenzoylecgonine methyl ester.

The compounds of this invention can be prepared by using the appropriate nor-tropane derivative. Where the nitrogen substituent is to be at the 8 position, an alpha-aralkyl halide having a nitro group in the appropriate position may be combined with a nor-tropane derivative so as to provide substitution at nitrogen. The nitro group may then be reduced to the amino group and diazotized according to conventional procedures. If the nitrogen substituent is to be at the 3 position, nitrated benzoic acid may be employed to form the ester with the 3-hydroxy tropane derivative and the nitro group reduced and then diazotized as required.

Antibodies

The preparation of antibodies specific for haptenic materials is a well established practice. A thorough description of the procedure may be found in Williams et. al, Methods in Immunology and Immunochemistry, Academic Press, New York and London, 1967, pages 197 to 385, particularly that portion beginning at 197 and ending at 254.

For preparation of antibodies to haptens, a hapten is conjugated to an antigenic material such as a polypeptide or protein, although polysaccharides, particularly containing amino sugars, can also be used.

The particular manner in which the hapten is bonded to the antigenic material, will depend on the functionalities which are available on the haptenic material and the antigenic material, the number of haptenic groups to be conjugated to the antigenic material, and the like.

Groups which find use include carboxy groups, which may be activated by employing the mixed carbonic acid anhydride or carbodiimide, imidates, diazo groups, alphahalo-ketones, and the like. Numerous procedures for the conjugation of a wide variety of haptens have been developed and published.

The antigenic conjugate may be injected in the fluid state; adsorbed to insoluble particles, such as alumina; or incorporated in matrix materials such as agar, calcium alginate, or Freund's adjuvants ("complete" or "incomplete", depending on whether mycobacteria are incorporated). The adsorption to various insoluble colloidal carriers is described in the aforementioned text, the carriers being illustrated by alumina, aluminum phosphate, blood charcoal and the like. Other materials include polyacrylamide gel, bentonite, and protein. As adjuvants, methylated bovine serum albumin and Freund's adjuvant find use. Complete Freund's adjuvant is a water-in-oil emulsion, using emulsion stabilizers such as lanolin, lanolin derivatives, e.g., Aquaphor, mannide mono-oleate and Arlacel A, available from Duke Laboratories, South Newark, Conn. The complete adjuvant is distinguished from the incomplete adjuvant, by having mycobacteria e.g., M.butyricum or M.tuberculosis. The adjuvants are commercially available from Difco Laboratories, Detroit, Mich.

Immunization can be carried out in a variety of ways with a number of different animals. For the most part, for commercial production of antibodies, relatively large animals are employed, such as equinine bovine, porcine, canine, ovine, caprine, rodentia, rabbits and hares. Of particular interest are horses, goats, sheep and cows, that is, the larger domestic animals, as well as rabbits.

The antigenic material may be injected interperitoneally, intramuscularly, subcutaneously, and the like. When employing Freund's adjuvants, usually in combination with saline, the amount of antigen employed will vary depending on the particular antigenic material and the number and period of prior injections. Usually, about 0.1 to 5 mg of antigenic material will be employed per one ml of solution. The total amount of antigenic material and solution will depend on the size, nature and weight of the animal employed. The initial injection will normally be at a number of sites, aliquots of the composition being employed.

The first injections of antigen serve to load the animal, and a period of time is allowed to pass before booster injections are introduced, normally two to five weeks. Bleeding may occur after each injection, so as to follow the formation of the desired antibody. Depending on the animal, bleedings can be carried out via heart puncture, the carotid artery or external jugular vein. The bleeding will usually be carried out about one week after an injection. The blood may then be combined with a small amount of sodium citrate, the mixture agitated and then the erythrocytes settled by standing or centrifugation. The plasma is drawn off and combined with calcium chloride, with clotting resulting. If necessary, thrombin may be added to enhance clotting. After breaking up the clot, the clot is compressed and serum is withdrawn and filtered. Various other procedures are known and can be employed.

The serum can be treated in various ways, depending on its subsequent use. The serum may be fractionated by employing ethanol, neutral salts such as ammonium sulfate or sodium sulfate, or the like. Alternatively, the serum may be chromatographed on various modified cellulose columns, e.g., diethylaminoethylcellulose or carboxymethylcellulose or, various physical means may be employed to concentrate the desired antibodies. Usually, the product will be dialyzed after dissolution in a buffer, filtered and then isolated.

Numerous preservatives can be employed to stabilize the antibodies and the antibodies will normally be stored at reduced temperatures.

The antibodies are primarily γ-globulin which are found to have a molecular weight of about 150,000. The antibodies will be specific for a particular spatial structure and polar- non-polar distribution. Varying structures deviating from an ideal structure will give different binding constants.

The following examples are offered by way of illustration and not by way of limitation.

(All temperatures not indicated are in Centigrade)

EXAMPLE A. Preparation of Cocaine and Cocaine Metabolite

Benzoyl Ecgonine Antibodies

Employing an antigen prepared in accordance with Example V, a sheep was injected with 4 cc of a solution with 0.5 cc aliquots at 4 subcutaneous sites and 1 cc intramuscularly in each hind leg, the solution was composed of 6 mg of the antigen in 1 ml saline and 3 ml complete Freund's adjuvant. Repeated injections were carried out on an approximately monthly basis of a solution containing 6 mg of the antigen, 1 ml saline, and 3 ml incomplete Freund's adjuvant.

The animals were bled about one week after each booster injection, either to follow the course of antibody formation or to obtain a supply of antibodies. About one week after the subject injection, the seventh injection, the animal was bled, approximately 500 cc of blood being mixed with 10 ml of 25% sodium citrate. The mixture was then centrifuged at 5,000 rpm for 20 minutes. The plasma was aspirated off and mixed with 10 ml of 25% calcium chloride. In order to enhance clotting, 2 NIH units of thrombin per ml of plasma was added and the mixture allowed to stand overnight at about 35° C.

The resulting clot was chopped up and the mixture centrifuged at 5,000 rpm for about 30–45 minutes at 5° C. The serum was then filtered through glass wool and isolated. To the serum was then added dropwise an equal volume of saturated ammonium sulfate in water with constant stirring at 4° C. After allowing the mixture to stand for one hour at that temperature, the mixture was centrifuged at 10,000 rpm for 30 minutes. The supernatant was decanted, and the precipitate (γ-globulin) was resuspended in 0.4 M, pH 8, borate buffer, containing 1 g/l of sodium azide and 0.1 g/l of Thimerosal. Initially, buffer is added of one-half the original serum volume and addition is continued until the precipitate is dissolved. The solution is then dialyzed continuously against 4 liters of the same buffer, after which it is filtered through a 2.2μ milipore filter. The product is then ready for use.

The antibody solution was found to have a binding constant of $2.3 \times 10^7$ with benzoyl ecgonine spin label.

EXAMPLE I

Preparation of para-Aminococaine and para-Aminobenzoylecgonine

A. Ecgonine hydrochloride (5.5 g, 24.8 mmoles) was dissolved in 35 ml of methanol (dried over 3-A Molecular sieves) and sat'd with dry hydrogen chloride keeping the receiver cool by immersion in an ice bath. Upon saturation the receiver was heated to 40° for 0.5 hr. and evaporated to dryness in vacuo. The white residue was stored at 0.05 mm Hg over potassium hydroxide for 16 hrs and then dissolved in the minimum amount of hot methanol to which 200 ml of boiling acetone was quickly added. After cooling in ice and filtering, there was obtained 4.2 g of white crystals, mp 214°-215° (lit. 214°-215°). Evaporation of the mother-liquor and repetition of the recrystallization yielded 0.8 g mp 212°-214°. Total yield was 86.3% of theory.

B. To 20 ml of cold saturated potassium carbonate solution in a 125 ml separator funnel was added a solution of 5.0 g (213 mmoles) ecgonine methyl ester hydrochloride in 5 ml water. The aqueous mixture was extracted with 4×60 ml of chloroform. The combined chloroform extracts were dried over anhydrous sodium carbonate and evaporated in vacuo. Pumping at 0.05 mm Hg for 15 min. yielded 4.0 g (93%) of TLC pure (20:1 CHCl$_3$:MeOH) ecgonine methyl ester.

The 4.0 g (20.1 mmoles) ecgonine methyl ester was dissolved in 50 ml dry benzene and then 30 ml benzene was distilled off. To the cooled distillation pot was added 3.65 ml triethylamine and a solution of 3.72 g freshly recrystalized p-nitrobenzoylchloride in 5 ml of dry benzene was added dropwise with cooling (ice bath) and agitation.

The resulting sludge was stirred at 40° to 1 hr under nitrogen. After cooling to room temperature the reaction mixture was taken up in 100 ml of chloroform and washed with 3×20 ml 5% aqueous sodium carbonate solution. The chloroform solution was dried over sodium carbonate, evaporated in vacuo and pumped (0.05 mm Hg) on overnight to yield 5.7 g (85.3%) of yellow oil [one spot on TLC (95/5, CHCl$_3$/MeOH)] and same $R_f$ as known sample but having a slight odor of triethylamine. No further attempt at purification was made and the product was used directly in next step.

C. To a solution of 6.5 g p-nitrococaine in 250 ml absolute methanol was added 600 mg 10% Pd/C under a N$_2$ blanket. The resulting mixture was hydrogenated at atmospheric pressure with rapid stirring and slight heating from the magnetic stirrer. After 0.5 hr. H$_2$ uptake ceased, [1.530 liters, calculated is 1.440 liters without correction for atmospheric pressure]. The catalyst was removed by suction filtration over a Celite pad in a fritted glass funnel (medium grade). The resulting clear solution was evaporated in vacuo to approximately 75 ml and heated to dissolve crystals which formed and then allowed to cool to room temperature, followed by cooling in ice and filtering to give 4.0 g white crystals, m.p. 188°-189°. The mother-liquor was concentrated to 3 ml, cooled in ice and filtered. After washing the crystals with 6 ml of cold methanol, there was obtained 1.2 g powdery crystals, m.p. 185°-188°. Total yield 88%.

Calc'd. for C$_{17}$H$_{22}$N$_2$O$_4$: % C, 64.13; % H, 6.96; % N, 8.80:

Fd: % C, 64.15; % H, 7.00; % N, 8.83.

D. p-Aminococaine (2.08) in 15 ml of water was refluxed with rapid stirring under nitrogen for 6 hrs. The solution was allowed to cool to room temperature and then cooled in ice and filtered. The crystals were washed with 5 ml cold water and dried at 0.05 mm Hg for 2 hrs to yield 1.2 g clear needle-like crystals, m.p. 287° (dec.). The compound slowly turns brown upon exposure to air and light. Recrystallization of 200 mg from 2 ml boiling water gave an analytically pure sample, Calc, %: C, 63.14; H, 6.62; N, 9.20: Found, %: C, 63.32; H, 6.62; N, 9.16.

EXAMPLE II

Preparation of N-(p-Aminobenzyl)nor-Ecgonine

A. A freshly prepared solution of 6.56 g (41.5 mmoles) potassium permanganate in 250 ml water was added dropwise over 3 hrs. to a stirred solution of 7.5 g (20.8 mmoles) benzoylecgonine tetrahydrate in one liter of water. The mixture was then stirred at room temperature for 16 hrs. After adding 50 ml of absolute methanol and stirring for an additional 4 hrs. the manganese dioxide was removed by gravity filtration using a well fluted filter. (It was often necessary to repeat the filtration to obtain a colorless filtrate.) To the colorless solution was added 55 meq. of hydrochloric acid and the acidic solution evaporated to dryness in vacuo. The residue was stored over potassium hydroxide pellets at 0.05 mm Hg overnight. The residue was then boiled with 50 ml of absolute ethanol and filtered to remove the potassium chloride. The filtrate was concentrated to 25 ml in vacuo and heated to redissolve the ppt., allowed to cool to room temperature and then cooled in ice and filtered. The crystals were washed with 5 ml of cold ethanol (abs.) and air-dried to yield 3.7 g nor-benzoylecgonine hydrochloride m.p. 213°-215°. An additional 0.7 g was obtained by dropwise addition of dry ethyl ether to the filtrate.

Both crops were combined and recrystalized from the minimum amount of boiling ethanol (abs.) to yield 4.0 g (54.0%) m.p. 229° (decomp.).

B. nor-Benzoylecgonine hydrochloride (3.5 g, 9.15 mmoles) in 45 ml 2 N hydrochloric acid was refluxed for 3 hrs. The cooled reaction mixture was washed with 3×30 ml ether, aqueous layer evaporated in vacuo and dried at 0.05 mm Hg over potassium hydroxide pellets for 16 hrs. The white residue was dissolved in anhydrous (3-A molecular sieves) methanol and saturated with hydrogen chloride keeping the receiver cooled in ice. The mixture was heated to 50° for 0.5 hr and stripped in vacuo, pumped on (0.1 mm Hg) for 1 hr and 30 ml ice cold saturated aqueous potassium carbonate solution added. The suspension was quickly extracted with 3×50 ml of chloroform, combined extracts dried over sodium carbonate and evaporated in vacuo. The oil was pumped on (0.05 mm Hg) for 20 min. to give 1.57 g (93%) straw colored oil TLC $R_f$ (0.15) CHCl$_3$/MeOH, 9/1, Silica gel.

C. To a solution of 7.0 g (38.0 mmoles) nor-ecgonine methyl ester in 50 ml ether was added a solution of 8.22 g (38 mmoles) p-nitrobenzyl bromide in 150 ml ether and 5.3 ml (38 mmoles) triethylamine. The resulting mixture was stoppered and stirred at room temperature for 2 days. Hydrochloric acid (1 N, 150 ml) was added and the mixture shaken. After separation, the aqueous layer was washed with 100 ml ether and made basic with excess aqueous sodium carbonate. The resulting oil was quickly taken up in 2×100 ml chloroform, dried over sodium carbonate, evaporated in vacuo and pumped on for 1 hr to yield 9.0 g (73%) of a pale yellow oil, which began to crystalize after 0.5 hr. The crystalline residue was recrystallized from 200 ml methylcyclohexane to give 7.2 g yellow crystals m.p. 78°-88°. Repeated crystallization failed to rase the melting point. The mother-liquor was stripped in vacuo, the residue taken up in 500 ml dry ether, and hydrogen chloride bubbled in until precipitation ceased. After filtering, the precipitate was washed with 100 ml dry ether and recrystalized from 2% methanol in chloroform three times. The white crystals were dried at 100° (0.05 mm Hg) for 10 hrs to give m.p. 210°–212° (decomp.).

Calc, %: C, 53.85; H, 5.93; N, 7.85; Cl, 9.95: Found, %: C, 51.69; H, 5.76; N, 7.50; Cl, 10.01.

D. To 3.50 g (10.9 mmoles) N-(p-nitrobenzyl) norecgonine methyl ester in 700 ml anhydrous 2% methanolic hydrogen chloride was added 350 mg 10% palladium on charcoal under a nitrogen blanket. The mixture was hydrogenated at atm. pressure and after 20 min. $H_2$ uptake ceased. Total uptake was 795 ml; calc. was 805 ml not taking pressure into account. The catalyst was removed using a Celite pad on a medium grade glass frit and washed with 100 ml methanol. The resulting clear solution was evaporated in vacuo to approximately 50 ml and cooled in ice. The ensuing white crystalline precipitate was filtered and washed with 25 ml ice cold methanol. After drying overnight at 0.05 mm Hg over potassium hydroxide pellets, 3.50 g (89%) of white crystals were obtained m.p. 220° (decomp.). Repeated crystallization failed to change the melting point.

The dihydrochloride (188 mg) was treated with 10 ml ice cold 5% aqueous potassium carbonate, quickly extracted with 3×40 ml chloroform, dried over sodium carbonate, evaporated in vacuo and pumped on to yield 150 mg light brown oil. TLC $R_f$ (0.2) ethyl ether on silica gel.

E. N-(p-aminobenzyl-) nor-ecgonine methyl ester dihydrochloride (2.0 g, 5.5 mmoles) in 30 ml 2 N hydrochloric acid was refluxed for 4 hrs, evaporated in vacuo and stored at 0.05 mm Hg over potassium hydroxide pellets overnight. The residue was dissolved in 3 ml of water and 100 of hot absolute ethanol was quickly added. Cooling in ice resulted in a fine white precipitate which was filtered and washed with 5 ml cold ethanol. The mother-liquor was evaporated in vacuo and the recrystalization repeated. Heating the material produces a yellow color.

Obtained 1.5 g (78%) slightly yellow crystals. $R_f$ 0.2 [conc. NH$_4$OH:EtOH, 1:7, on silica gel] m.p. 235° (decomp.).

Calc, %: C, 51.59; H, 6.35; N, 8.02; Cl, 20.30: Found, %: C, 48.71; H, 6.16; N, 7.63; Cl, 19.53.

EXAMPLE III

Conjugation of N-(p-Aminobenzyl)nor-Ecgonine Methyl Ester with Bovine Serum Albumin (BSA)

To 300 mg (0.83 mmoles) N-(p-aminobenzyl)norecgonine methyl ester dihydrochloride in 5 ml 0.3 N hydrochloric acid at 0° was added a solution of 57 mg (0.83 mmoles) sodium nitrite in ice cold water. After 10 min. the diazonium salt solution was dropwise added over a period of 5 min. to a well cooled (ice bath), vigorously stirring solution of 1 g BSA in 50 ml water at pH 9 (adjusted with 2 N sodium hydroxide). The pH of the reaction was kept constant by intermittent addition of 2 N sodium hydroxide and continuous monitoring with a pH meter. The solution was stirred at 0° for 20 min. after addition was complete, followed by addition of 100 mg urea and 100 mg beta-naphthol. The dark red solution was desalted on a 100×5 cm Sephadex G-25 (med.) column and lyophilized to give 1.10 g orange conjugate.

EXAMPLE IV

Conjugation of N-(p-Aminobenzyl)nor-Ecgonine with Bovine Serum Albumin

To a solution of 290 mg (0.83 mmoles) N-(p-aminobenzyl)-nor-ecgonine dihydrochloride in 5 ml 0.3 N hydrochloric acid at 0° was added a solution of 57 mg (0.83 mmoles) sodium nitrite in 20 ml water at 0°. After 10 min. the diazonium salt solution was added dropwise over 5 min. to a vigorously stirring solution of 1.0 g BSA in 50 ml water at 0° and pH 9. The pH of the reaction was kept constant by intermittent addition of 2 N sodium hydroxide and continuous monitoring with a pH meter. After stirring for 20 min. at 0°, 100 mg urea and 100 mg beta-naphthol was added and the dark red solution was desalted on a 100×5 cm Sephadex G-25 (med.) column using pH 9 water (NH$_4$OH) to elute. The desalted solution was lyophilized to yield 1.0 g orange conjugate.

EXAMPLE V

Conjugation of para-Aminobenzoylecgonine with Bovine Serum Albumin (BSA)

To a solution of 95 mg (0.313 mmoles) para-aminobenzoylecogonine in 2 ml 0.2 N hydrochloric acid was added dropwise a solution of 21.5 mg (0.313 mmole) sodium nitrite in 2.0 ml water keeping all solutions cooled to 0° in an ice bath. The diazotized solution was added dropwise over a period of 5 min. to a well cooled (ice bath) vigorously stirred solution of 300 mg BSA in 20 ml water at pH 9 (adjusted with 0.1 N sodium hydroxide). The pH of the reaction was kept constant by intermittent addition of 0.1 N sodium hydroxide and continuous monitoring with a pH meter. The mixture was allowed to stir for 2 hrs at 0° C. after addition was complete. Urea (100 mg) was added and the solution allowed to come to room temperature, which was then desalted on a 100 cm×5 cm Sephadex G-25 (med.) column and lyophilized to yield 290 mg light yellow conjugate.

EXAMPLE VI

Preparation of N-(p-Aminobenzyl)nor-Ecgonine Methyl Ester Conjugate with 1-Oxyl-2,2,5,5-Tetramethyl Pyrrolidinyl-3-Formic Acid To a solution of 187 mg (1.0 mmole) 3-carboxy-2,2,5,5-tetramethyl pyrrolidine-1-oxyl in 5 ml dry DMF at 0° was added 139 μl (1.0 mmole) triethylamine and 126 μl (1.0 mmole) isobutylchloroformate and the mixture stirred under N$_2$ for 45 min. at 0°. To this mixed anhydride solution was added a suspension of 363 mg (1.0 mmole) N-(p-aminobenzyl)nor-ecgonine methyl ester dihydrochloride and 417 μl (3.0 mmoles) triethylamine in 10 ml dry DMF at 0°. The resulting mixture was stirred at 0° for 2 hrs under N$_2$, then at room temperature overnight. The DMF was evaporated in vacuo, residue taken up in 10 ml water, basified with aqueous sodium carbonate and quickly extracted with 3×20 ml ether. The combined ethereal extracts were dried over sodium carbonate stripped in vacuo and pumped on (0.05 mm Hg) for 2 hrs. The residue was dissolved in 5 ml benzene and 15 ml ether added. The resulting precipitate was filtered and the supernatant stripped in vacuo to yield 100 mg (22%) yellow crystals. TLC $R_f$ 0.3, 5% MeOH/EtOH, on silica gel.

M+458. M.P. 83°–87° I.R.-1720 cm$^{-1}$, 1690 cm$^{-1}$.

EXAMPLE VII

Preparation of para-Aminococaine Conjugate to 1-Oxyl-2,2,5,5-Tetramethyl Pyrrolidinyl-3-Formic Acid To a mixture of 374 mg (2.0 mmoles) 3-carboxy-1-oxyl-2,2,5,5-tetramethyl pyrrolidine and 292 µl (2.05 mmoles) triethylamine in 5 ml anhydrous ethyl ether was added 145 µl (2.0 mmoles) thionyl chloride and the resulting mixture stirred at room temperature for 0.5 hr. under nitrogen. The ether was removed by heating to 40° for several mins. and a solution of 636 mg (2.0 mmoles) para-aminococaine and 292 µl (2.05 mmoles) triethylamine in 20 ml anhydrous ethyl ether was added and the mixture refluxed under nitrogen for 0.5 hr. The mixture was cooled in ice and filtered. The filtrate was washed with 10 ml of 5% aqueous sodium carbonate solution and dried over anhydrous sodium carbonate. The dried ethereal solution was then poured into 200 ml of petroleum ether and the resulting pale yellow precipitate filtered and washed with 50 ml of petroleum ether. The precipitate was taken up in 5 ml of benzene and the precipitation procedure was repeated. The resulting pale yellow solid was dried at 0.05 mm Hg over phosphorus pentoxide at room temperature overnight to yield 100 mg. m.p. 208°–210°.

Calc, %: C, 64.18; H, 7.46; N, 8.64; Found, %: C, 64.18; H, 7.57; N, 8.44.

EXAMPLE VIII

Preparation of N-para-(O$^3$-Ecgoninyloxycarbonylphenyl) 1-Oxyl-2,2,5,5-Tetramethyl Pyrrolidinyl-3-Formamide A solution of 70 mg of N-(para-cocainyl) 1-oxyl-2,2,5,5,-tetramethyl pyrrolidinyl-3-formamide in 8 ml of water and 8 ml of dioxane was refluxed for 48 hrs under nitrogen. At the end of this time, thin layer chromatography (silica; 1:1 chloroform:methanol) indicated substantially complete reaction. The reaction mixture was evaporated to dryness in vacuo while maintaining the temperature below 40°. The residue was purified by preparative thin layer chromatography and removed from the silica by washing with methanol. The evaporated residue was freed of silica by trituration with acetone, followed by filtration. The pure product was isolated as a viscous oil in 70% yield (48 mg). Calc'd. for $C_{25}H_{34L}N_3O_6 \cdot H_2O$: C-61.21%, H-7.40%, N-8.57%; Fd: C-61.28%, H-7.38%, N-8.34%.

EXAMPLE IX p-Diazobenzoylecgonine Conjugate of Lysozyme p-Aminobenzoylecgonine (50 mg) in 1 ml of 0.2 N HCl at 0° was added dropwise to 11.3 mg NaNO$_2$ in 1 ml of H$_2$O at 0°. A yellow color developed. The resulting diazonium salt was added dropwise over 5 min. to a solution of 200 mg lysozyme (Miles 6× recryst.) in 10 ml water at 0°, pH 9.0. A red color developed, and some precipitate appeared. The pH was maintained at 9.0 with stirring, 1.5 hrs at 0°. The mixture was then centrifuged.

The supernatant was yellow, and the precipitate red. The precipitate was readily dissolved in 8 M urea. Both fractions were dialyzed against H$_2$O.

Assays

The assay employed was a spin label immunoassay. The γ-globulin employed was prepared from serum by ammonium sulfate precipitation and dialysis of the redissolved precipitate against 0.4 M borate, pH 8 as described in Example A. All assays were performed at a final buffer concentration of 0.18 M borate buffer. A solution was prepared having a ratio of antibody sites to moles of spin label of 1:1.5. Twenty µl of sample was employed with 10 µl of the γ-globulin spin label combination, with the spin label having a final concentration in the assay mixture of $2.64 \times 10^{-6}$ M. The serum had a concentration of binding sites of $4.7 \times 10^{-5}$ and a binding constant of $8.8 \times 10^6$ per mole.

Ninety-nine urines from a normal population were tested by adding 20 µl of urine to 10 µl of the γ-globulin-spin label (Example VIII) solution. The background cutoff was found to be 1.8 µg equivalents of benzoylecgonine per ml. Seventeen urine samples were taken from people who had previously snuffed cocaine and were frozen in small aliquots. These samples were assayed some time later and 8 of the 11 samples where cocaine had been snuffed 12 to 24 hours before taking a sample were found to be positive.

In carrying out the enzyme assay, the product (Example IX) obtained from the precipitate and dialyzed was employed and diluted 250 fold. The assay is carried out by employing a bacterial suspension of M. luteus; 0.2 ml of a suspension of 300 mg of the bacteria in 400 ml of 0.025 M, pH 6, Tris-maleate buffer. First, the bacterial suspension is introduced into the assay vessel. When testing a sample, 50 µl of the sample is then introduced. This is followed by 50 µl of antibody solution ($2.62 \times 10^{-5}$ M binding sites $5.7 \times 10^6$ binding constant) in 0.025 M, pH 6, Tris-maleate buffer and the transfer made quantitative by washing with 325 µl of the same buffer solution. The benzoyl ecgonine conjugate to lysozyme (50 µl) is then added to give a binding site to benzoyl ecgonine ratio of 1:1 and 325 µl of buffer used to insure quantitative transfer. The supernatant of the dialysis product of the precipitate of the benzoyl ecgonine conjugate to lysozyme was diluted 250 fold and employed in the test. The results were read by observing the decrease in optical density at 436 nm for 40 seconds at 36°. The results are reported in arbitrary units as OD/min. In the absence of antibody, the rate was 168–171 OD/min. When the antibody was added, the rate dropped to 45 OD/min. With 50 µl of a solution of 0.5 µg/ml benzoyl ecgonine the rate was found to be 50,52 OD/min. With 50 µl of a 5 µg/ml benzoyl ecgonine solution, the rate was 70,75 OD/min., while the 50 µl of 50 µg/ml concentration, the rate was 122,125 OD/min.

The compounds of this invention are particularly advantageous for use in preparing reagents for accurate determinations of cocaine and metabolites in a variety of immunoassays. Antibodies are obtained which have high specificity and strong binding constants to cocaine and its metabolites. The compounds when combined with detector molecules, such as stable free radicals and enzymes, provide reagents which can compete with cocaine and its metabolites to permit accurate determination of cocaine and its metabolites at extremely low concentrations. Reagents can be stored and shipped for commercially reasonable periods of time.

What is claimed is:

1. An antibody formed in response to an antigenic poly(amino acid) of the formula:

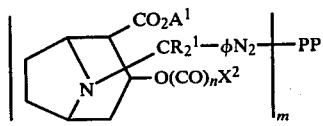

wherein:
φ is phenyl;
$A^1$ is hydrogen or methyl;
$R^1$ is hydrogen or alkyl of from 1 to 3 carbon atoms;
$X^2$ is hydrogen or phenyl;
n is zero when $X^2$ is hydrogen and one when $X^2$ is phenyl;
PP is antigenic poly(amino acid); and
m ranges from one to the molecular weight of PP divided by 500.

2. An antibody according to claim 1 wherein $A^1$ and $R^1$ are both hydrogen.

3. An antibody according to claim 1, wherein $A^1$ is methyl and $R^1$ is hydrogen.

4. An antibody formed in response to an antigenic poly(amino acid) of the formula:

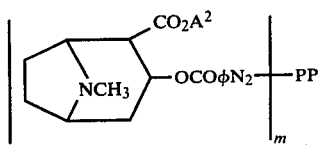

wherein:
φ is phenyl;
$A^2$ is hydrogen or methyl;
PP is polypeptide; and
m ranges from 1 to the molecular weight of PP divided by 500.

5. An antibody according to claim 4, wherein $A^2$ is hydrogen.

* * * * *